United States Patent [19]

Rosenberg

[11] Patent Number: 5,360,339
[45] Date of Patent: Nov. 1, 1994

[54] DENTAL PROPHY CUP HAVING A PASTE-DISTRIBUTING CHANNEL ARRANGEMENT

[76] Inventor: Neil A. Rosenberg, 32 Equator Dr., Nantucket, Mass. 02554

[21] Appl. No.: 203,586

[22] Filed: Mar. 1, 1994

[51] Int. Cl.$^5$ .............................................. A61C 3/06
[52] U.S. Cl. ................................................... 433/165
[58] Field of Search ................................. 433/125, 166

[56] References Cited

U.S. PATENT DOCUMENTS

| | | | |
|---|---|---|---|
| 2,017,881 | 10/1935 | Wiseman | 433/166 |
| 2,093,006 | 9/1937 | Chott | 433/166 |
| 2,135,933 | 11/1938 | Blair | 433/166 |
| 2,226,145 | 12/1940 | Smith | 433/166 |
| 2,738,528 | 3/1956 | Fridge, Sr. | 433/166 |
| 2,789,352 | 4/1957 | Wiseman | 433/166 |
| 3,163,934 | 1/1965 | Wiseman | 433/125 |
| 3,599,333 | 8/1971 | Muhler | 433/166 |
| 4,259,071 | 3/1981 | Warden et al. | 433/166 |
| 4,854,870 | 8/1989 | Kofod | 433/166 |
| 4,929,180 | 5/1990 | Moreschini | 433/166 |

*Primary Examiner*—Cary E. O'Connor
*Attorney, Agent, or Firm*—Burns, Doane, Swecker & Mathis

[57] ABSTRACT

A dental prophy cup comprises a flexible body having a cavity formed therein. A rear end of the cavity includes a paste reservoir for storing an abrasive paste. Paste-delivery channels extend forwardly from the reservoir and intersect front and rear circumferentially extending paste-distribution channels. Under the action of centrifugal force occurring during a tooth-cleaning procedure, paste is fed forwardly along the delivery channels and is distributed within the distribution channels. Between the channels is disposed a pattern of ridges which are capable of flexing relative to one another to conform to the shape of a tooth surface.

17 Claims, 2 Drawing Sheets

DENTAL PROPHY CUP HAVING A PASTE-DISTRIBUTING CHANNEL ARRANGEMENT

BACKGROUND OF THE INVENTION

The present invention relates to a dental prophy cup used in dental prophylaxis procedures and, in particular, to a novel configuration and construction of such a cup.

A dental prophylaxis procedure typically involves the application of an abrasive paste (i.e., a paste containing abrasive particles) to a tooth surface upon which pressure and rotational motion are applied. The removal of plaque, calculus and stains is facilitated by the resultant abrasion at the interface between the abrasive particles and tooth surface.

The pressure and rotational motion are applied to the abrasive paste by means of a prophy cup which comprises a flexible cup-shaped element of about one-quarter inch diameter. A rear portion of the cup is mounted on a drive shaft which rotates the cup at high speed, e.g., about 1500 rpm. The front portion of the cup forms an internal cavity which receives the paste. The wall of the cavity typically includes a plurality of fins extending in a front-to-rear direction. An operator presses the front portion of the cup against a tooth following the insertion of abrasive paste into the cavity. The paste serves as a lubricant, and the abrasives in the paste function to abrade away plaque, calculus, and stains from the tooth surfaces.

This procedure has traditionally exhibited certain shortcomings. For example, the centrifugal force generated by a prophy cup rotating at 1500 rpm causes the paste to be displaced from the cavity. In fact, the amount of paste retained at the interface between the cup and tooth surface after one second (25 rotations) is a small fraction of the initial volume. This diminishing of paste results in reduced abrasion and cleaning performance.

An additional shortcoming relates to the geometry of the cup itself. In that regard, prophy cups are designed to be flexible, so that as the operator presses the cup against a tooth surface, the outer annular rim of the cup flexes in order to conform to the shape of the tooth surface, and thereby increase the area of surface contact therebetween. However, the presence of fins along the cavity wall tends to stiffen the cup, so that the ability of the cup to flex and conform to the curvature of the tooth surface is reduced. This makes it difficult for the operator to control the magnitude and placement of abrasion.

Therefore, it would be desirable to provide a dental prophy cup which increases the residence time and degree of distribution of abrasive paste therein.

It would also be desirable to increase the flexibility of the cup to enable the cup to better conform to the shape of the tooth.

SUMMARY OF THE INVENTION

The present invention relates to a dental prophy cup comprising a body having a rear mounting portion adapted to be mounted on a rotary handpiece for rotation about a longitudinal axis of rotation, and a front tooth-engaging portion formed of an elastomeric material and including a cavity for receiving an abrasive paste. The cavity expands toward a front end of the body. The cavity is defined by a surface in which there is formed a channel arrangement comprised of a paste-delivery channel extending forwardly from a rear portion of the cavity, and a circumferentially extending paste-distribution channel spaced rearwardly from a front end of the body. The paste-delivery channel intersects the paste-distribution channel and terminates at the paste-distribution channel such that paste is induced to flow along the channel arrangement under the urging of centrifugal force during rotation of the body. The paste is retained within the cavity for an extended period, and is amply distributed within the cavity.

Preferably, there is a plurality of paste-delivery channels spaced circumferentially apart, and a plurality of paste-distribution channels spaced longitudinally apart.

The channel arrangement forms a network of ridges. Each ridge has a tooth-engaging surface which generally faces the axis of rotation when the cup is in a relaxed state. A front set of ridges is spaced forwardly of a rear set of ridges. The tooth-engaging surfaces of the rear set of ridges is situated closer to the axis of rotation than the tooth-engaging surfaces of the front set of ridges. Each tooth-engaging surface has a front edge located farther from the axis of rotation than a rear edge thereof.

The cup body is preferably formed of polyisoprene.

BRIEF DESCRIPTION OF THE DRAWINGS

The objects and advantages of the invention will become apparent from the following detailed description of a preferred embodiment thereof in connection with the accompanying drawings in which like numeral designate like elements and in which.

DETAILED DESCRIPTION OF A PREFERRED EMBODIMENT OF THE INVENTION

Figure 1:
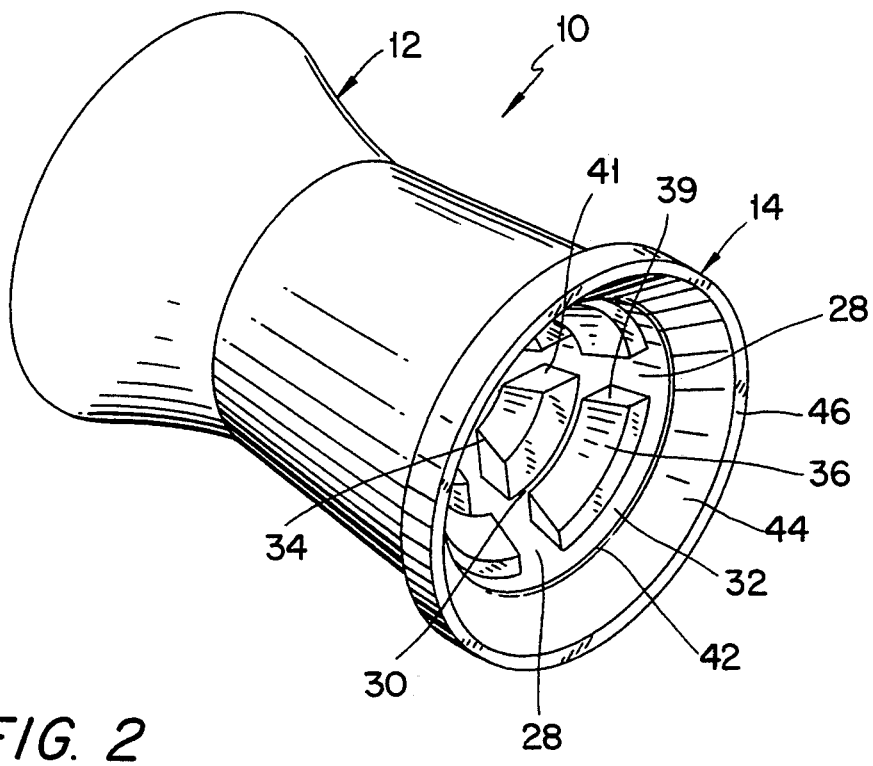
FIG. 1 is a front perspective view of a dental prophy cup according to the present invention.
Figure 2:
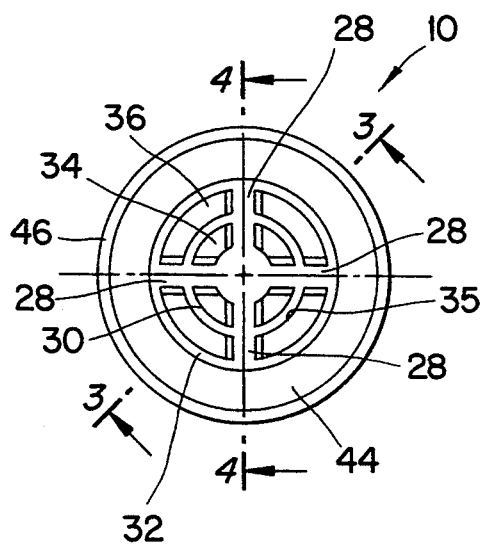
FIG. 2 is a front end view of the prophy cup depicted in FIG. 1.

A dental prophy cup 10 depicted in FIGS. 1–4 comprises a body formed of a highly flexible material, preferably polyisoprene. A rear mounting portion 12 of the cup would be configured for being mounted to the drive shank of a rotary handpiece (not shown) by screwing, latching, or snap-on, as is conventional. The depicted mounting portion 12 includes a hole 14 leading to an enlarged pocket 16 into which the free end of the shank is inserted by snap-fit in the usual manner.

Projecting forwardly from the mounting portion 12 is a tooth-cleaning portion 20 which forms a cavity 22 configured to be symmetrical about a central axis of rotation A of the cup. The cross-section of the cavity expands toward the front of the cup. The cavity 22 is defined by an internal surface 24 which forms a paste reservoir 26 at a rear end of the cavity. Disposed in the surface 24 are four paste-delivery channels 28 each extending longitudinally forwardly and radially outwardly from the paste reservoir 26, and two longitudinally spaced, circumferentially extending paste-distribution channels 30, 32.

Those channels 28, 30, 32 cooperate to form two sets of circumferentially extending ridges 34, 36. A rear set of the ridges 34 is situated longitudinally rearwardly from a front set of the ridges 36. There are four evenly spaced rear ridges 34, each bordered by two paste-delivery channels 28 and a rear one of the paste-distribution channels 30. It will be appreciated that front walls of the rear paste-distribution channel 30 are formed by rear walls 35 of the front ridges 36.

There are four evenly spaced front ridges 36, each bordered by two paste-delivery channels 28 and a front one of the paste-distribution channels 32. The rear ridges 34 form tooth-engaging surfaces 38, and the front ridges 36 form tooth-engaging surfaces 40.

The paste-delivery channels 28 are forwardly divergent, whereby the front ridges 36 are longer than the rear ridges 34 in the circumferential direction. Also, the front ridges 36 are spaced farther from the axis A than the rear ridges 34 when the cup is in a relaxed (unflexed) condition. Thus, it will be appreciated that the paste-delivery channels 28 become progressively shallower toward their front ends.

Figure 3:
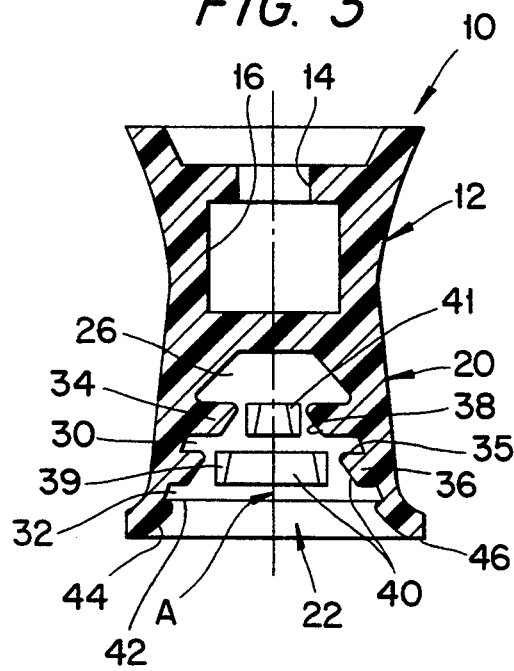
FIG. 3 is a longitudinal sectional view taken along the line 3—3 in FIG. 2.
Figure 4:
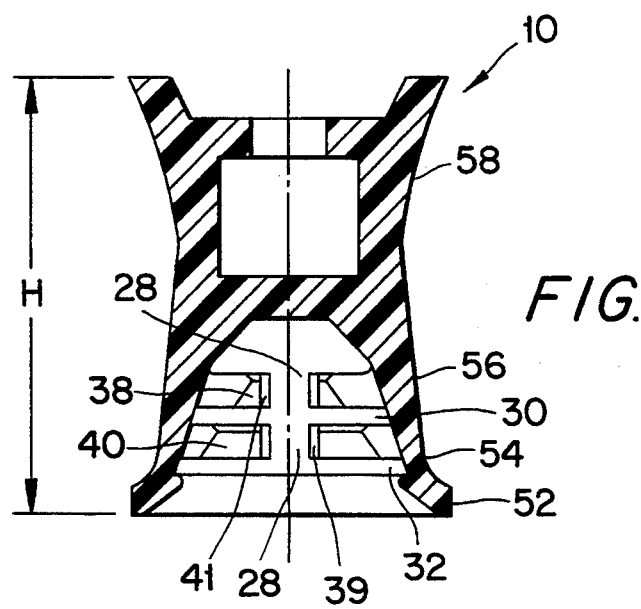
FIG. 4 is a longitudinal sectional view taken along the line 4—4 in FIG. 2.

The two circumferentially spaced side surfaces 39 of each of the front ridges 36 are inclined so as to be radially inwardly convergent to A (as can be seen in FIG. 1). The same is true of the side surfaces 41 of the rear ridges 34. Each of the tooth-engaging surfaces 38, 40 of the rear and front ridges 34, 36, is inclined such that a rear edge thereof is located closer to the axis A than is a front edge thereof, when the body is in a relaxed condition (as can be seen in FIG. 3).

The front paste-distribution channel 32 is circumferentially continuous, whereas the rear paste-distribution channel 30 is interrupted circumferentially by the paste-delivery channels. The paste-delivery channels 28 thus terminate at the front paste-distribution channel 32, and the front ends of the paste-delivery channels 28 are closed by a circumferentially continuous front wall 42 of the front paste-distribution channel 32.

Extending forwardly from the wall 42 is an outwardly flared surface 44 which terminates forwardly at the radially inner edge of a forwardly facing rim surface 46.

An external surface of the cup body includes a cylindrical portion 52 (see FIG. 4) extending rearwardly from a radially outer edge of the rim surface 46, and a concave portion 54 extending from a rear end of the cylindrical portion 52 to a front end of a generally frusto-conical portion 56. The latter narrows rearwardly toward an external surface 58 of the mounting portion 12.

Figure 5:
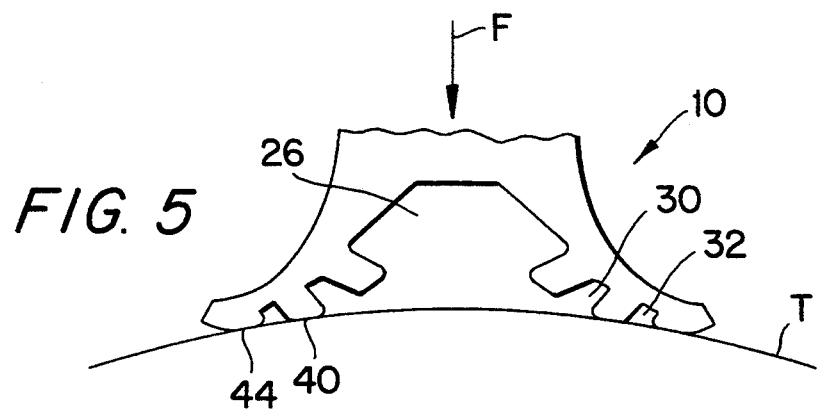
FIG. 5 is a schematic view depicting the flexing of the prophy cup under moderate pressure.
Figure 6:
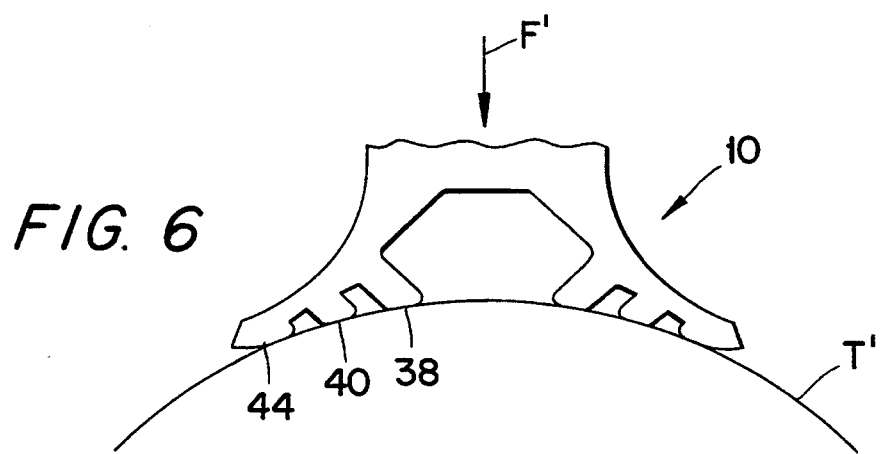
FIG. 6 is a view similar to FIG. 5 when the prophy cup is subjected to a greater force.

In use, the cavity 22 is filled with an abrasive paste, the cup is pressed against a patient's tooth surface T (FIG. 5), and the cup is rotated (preferably at 1500-2000 rpm). During the application of a normal (moderate) force F to the cup (e.g., 0.5 pounds), the tooth-engaging portion 14 flexes to cause the circumferentially continuous front surface 44 and the surfaces 40 of the front ridges 36 to contact the tooth surface T which is from small to moderate curvature, as shown in FIG. 5. When engaging a tooth surface T' which is from moderate to severe curvature (see FIG. 6), a higher force F' is applied to the cup to further cause the tooth-engaging surface 14 to flex so that the surfaces 38 of the rear ridges 34 also contact that tooth surface T', as shown in FIG. 6.

It will be appreciated that the flexing of the cup is facilitated by the presence of the channels 28, 30, 32 which reduce the thickness of the cup body and define annular bending fulcrums about which certain portions of the cup body can flex in order to enable the surfaces 44 and 40 (and optionally surface 38) into engagement with the tooth surface. In other words, the cup is better able to confirm to the curvature of the tooth surface.

As the cup rotates, the abrasive paste compressed between the cup and tooth abrades away stains and adherent materials such as plaque and calculus.

Centrifugal force causes the paste to travel radially outwardly, and thus longitudinally forwardly, due to the forwardly expanding shape of the cavity surface 24. Some of the paste disposed within the cavity is quickly expelled from the cup by the centrifugal force. Gradually, replacement paste flows forwardly from the reservoir 26 along the paste-delivery channels 28 and enters the paste-distribution channels 30, 32 for circumferential distribution. Paste which reaches the front paste-distribution channel 32 is obstructed from further forward travel by the front wall 42 thereof. Accordingly, it is ensured that an ample amount of generally uniformly distributed paste resides in the cavity 22 for an extended period.

The cup is of reduced height H, e.g., 10% shorter than standard prophy cups, so that the cup is more accessible to hard-to-reach areas. The cup is preferably 0.34 inch in height H in a screw-on cup (on 0.32 inch in height H in a snap-on cup), and 0.25 in maximum diameter (front end). Standard prophy cups are 0.375 inches in height.

As noted earlier, the cup body is preferably formed of polyisoprene. That material can exhibit various degrees of hardness, depending upon its composition, as is known to those skilled in the art. For cleaning regular stains from teeth, there could be used a prophy cup according to the present invention having a durometer value (i.e., hardness) of 30-40; for cleaning heavy stains, such as tobacco stains, the prophy cup could have a durometer value greater than 50 (e.g., 50-70).

In accordance with the present invention, a prophy cup is provided which effectively distributes abrasive paste within the cavity and impedes the centrifugally-induced loss of the paste from the cavity. This serves to conserve paste, and also to conserve time by reducing the number of occasions on which the operator must interrupt a tooth-cleaning operation to re-supply the prophy cup with paste. Also, it is less likely that at any given moment the operator will be performing a cleaning operation with an insufficient amount of paste in the cup.

Also, the body is uniquely flexible, due to the presence of the longitudinal and circumferential channels, allowing the cup to more closely conform to the curvature of a tooth surface.

By increasing the paste retention time and distribution, and enhancing the area of tooth contact, the overall abrasiveness (and thus effectiveness) of the prophy cup is increased.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. A dental prophy cup comprising a body having a rear mounting portion adapted to be mounted on a rotary handpiece for rotation about a longitudinal axis of rotation, and a front tooth-engaging portion formed of an elastomeric material and including a cavity for receiving an abrasive paste, said cavity expanding toward a front end of said body, said cavity being defined by a surface having formed therein a channel arrangement comprising a paste-delivery channel extending forwardly from a rear portion of said cavity, and a circumferentially extending paste-distribution channel spaced rearwardly from a front end of said body, said paste-delivery channel intersecting and terminating at said paste-distribution channel such that paste is induced to flow within said channel arrangement under the urging of centrifugal force during rotation of said body.

2. A dental prophy cup according to claim 1, wherein said paste-distribution channel includes a circumferentially continuous front wall.

3. A dental prophy cup according to claim 1, wherein there are a plurality of said paste-delivery channels spaced circumferentially apart, and a plurality of said paste-distribution channels spaced longitudinally apart.

4. A dental prophy cup according to claim 3, wherein there are four said paste-delivery channels spaced apart by ninety degrees.

5. A dental prophy cup according to claim 1, wherein said paste-distribution channel constitutes a front paste-distribution channel, said cavity further including a rear paste-distribution channel disposed rearwardly of said front paste-distribution channel and extending circumferentially, said rear paste-distribution channel being interrupted circumferentially by said paste-delivery channel.

6. A dental prophy cup according to claim 5, wherein said paste-delivery channel becomes progressively shallower in a forward direction.

7. A dental prophy cup according to claim 5, wherein there are a plurality of said paste-delivery channels spaced circumferentially apart, said paste-delivery and paste-distribution channels forming therebetween front and rear sets of circumferentially extending ridges, said ridges of each set being spaced circumferentially apart by said paste-delivery channels, said paste-delivery channels being forwardly divergent such that said ridges of said rear set are shorter than said ridges of said front set in the circumferential direction.

8. A dental prophy cup according to claim 7, wherein each of said front and rear ridges has a tooth-engaging surface generally facing said axis of rotation, a front edge of each of said tooth-engaging surfaces being spaced farther from said axis than a rear edge thereof when said body is in a relaxed condition.

9. A dental prophy cup according to claim 8, wherein each of said front and rear ridges has a tooth-engaging surface generally facing said axis of rotation, said tooth-engaging surfaces of said rear ridges being disposed closer to said axis than said tooth-engaging surfaces of said front ridges.

10. A dental prophy cup according to claim 1, wherein each of said front and rear ridges has a tooth-engaging surface generally facing said axis of rotation, said tooth-engaging surfaces of said rear ridges being disposed closer to said axis than said tooth-engaging surfaces of said front ridges.

11. A dental prophy cup according to claim 1, wherein said cavity includes a paste reservoir disposed at a rear end thereof, said paste-distribution channel disposed forwardly of said reservoir, said paste-delivery channel extending from said reservoir to said paste-distribution channel.

12. A dental prophy cup according to claim 1, wherein said tooth-engaging portion is formed of polyisoprene.

13. A dental prophy cup according to claim 1, wherein a longitudinal height of said cup is no greater than 0.34 inches.

14. A dental prophy cup comprising a body having a rear mounting portion adapted to be mounted on a rotary handpiece for rotation about a longitudinal axis of rotation, and a front tooth-engaging portion formed of an elastomeric material and including a cavity for receiving an abrasive paste, said cavity including a paste reservoir located at a rear end thereof, said cavity gradually expanding toward a front end of said body, said cavity including a plurality of paste-delivery channels extending forwardly from said reservoir, and front and rear circumferentially extending paste-distribution channels, said front distribution channel being circumferentially continuous and spaced rearwardly from a front end of said body, said paste-delivery channels intersecting said front and rear paste-distribution channels and terminating at said front paste-distribution channel, said paste-delivery and paste-distribution channels forming therebetween front and rear sets of circumferentially extending ridges, said ridges of each set being spaced apart circumferentially by said paste-delivery channels, each of said ridges forming a tooth-engaging surface generally facing said axis of rotation, said tooth-engaging surfaces of said rear ridges being disposed closer to said axis than said tooth-engaging surfaces of said front ridges, a front edge of each tooth-engaging surface being spaced farther from said axis than a rear edge thereof when said body is in a relaxed condition.

15. A dental prophy cup according to claim 14, wherein said paste delivery channels are forwardly divergent such that said front ridges are longer in the circumferential direction than said rear ridges.

16. A dental prophy cup according to claim 14, wherein said tooth-engaging portion is formed of polyisoprene.

17. A dental prophy cup according to claim 12, wherein a longitudinal height of said cup is no greater than 0.34 inches.

* * * * *